(12) United States Patent
Mahajan et al.

(10) Patent No.: US 12,383,749 B2
(45) Date of Patent: Aug. 12, 2025

(54) SYSTEMS AND METHODS FOR PRESENTING ARRHYTHMIA EPISODES

(71) Applicant: Cardiac Pacemakers, Inc., St. Paul, MN (US)

(72) Inventors: Deepa Mahajan, North Oaks, MN (US); David L. Perschbacher, Blaine, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 417 days.

(21) Appl. No.: 17/962,746

(22) Filed: Oct. 10, 2022

(65) Prior Publication Data

US 2023/0040827 A1 Feb. 9, 2023

Related U.S. Application Data

(63) Continuation of application No. 16/260,947, filed on Jan. 29, 2019, now Pat. No. 11,491,337.

(Continued)

(51) Int. Cl.
*A61B 5/346* (2021.01)
*A61B 5/00* (2006.01)
(Continued)

(52) U.S. Cl.
CPC .......... *A61N 1/37247* (2013.01); *A61B 5/361* (2021.01); *A61B 5/364* (2021.01);
(Continued)

(58) Field of Classification Search
CPC .......... A61B 5/35; A61B 5/7475; A61B 5/364
See application file for complete search history.

(56) References Cited

U.S. PATENT DOCUMENTS 8,521,269 B1 8/2013 Gunderson et al.
11,491,337 B2 * 11/2022 Mahajan ............... A61B 5/361
(Continued)

FOREIGN PATENT DOCUMENTS

CN 111936201 A 11/2020
CN 111936201 B 4/2024
(Continued)

OTHER PUBLICATIONS

"Chinese Application Serial No. 201980024133.3, Response to Examiner Telephone Interview filed Jan. 23, 24", w/ English claims, 73 pgs.
(Continued)

*Primary Examiner* — Eric D. Bertram
(74) *Attorney, Agent, or Firm* — Schwegman Lundberg & Woessner, P.A

(57) ABSTRACT

Systems and methods for managing machine-generated alert notifications of medical events detected from one or more patients are described herein. An embodiment of a data management system may receive an adjudication of a medical event episode including an episode characterization. A storage unit stores an association between one or more episode characterizations and corresponding detection algorithms for detecting a medical event having respective episode characterizations. An episode management circuit may detect from a subsequent episode, using the stored association, a medical event having an episode characterization of at least one medical event episode presented for adjudication, and schedule presenting at least a portion of the subsequent episode based on the detection.

20 Claims, 6 Drawing Sheets

Related U.S. Application Data

(60) Provisional application No. 62/625,197, filed on Feb. 1, 2018.

(51) Int. Cl.
    *A61B 5/361*      (2021.01)
    *A61B 5/364*      (2021.01)
    *A61N 1/362*      (2006.01)
    *A61N 1/37*      (2006.01)
    *A61N 1/372*      (2006.01)

(52) U.S. Cl.
    CPC .......... *A61B 5/7475* (2013.01); *A61N 1/3621* (2013.01); *A61N 1/3627* (2013.01); *A61N 1/3702* (2013.01); *A61N 1/3704* (2013.01)

(56) References Cited

U.S. PATENT DOCUMENTS

| | | | |
|---|---|---|---|
| 2006/0247548 A1 | 11/2006 | Sarkar et al. | |
| 2010/0106036 A1 | 4/2010 | Dong et al. | |
| 2012/0190969 A1 | 7/2012 | Kameli | |
| 2013/0085403 A1 | 4/2013 | Gunderson et al. | |
| 2013/0211855 A1 | 8/2013 | Eberle et al. | |
| 2016/0045125 A1 | 2/2016 | Krueger et al. | |
| 2016/0278659 A1* | 9/2016 | Kaib | A61B 5/361 |
| 2017/0196457 A1 | 7/2017 | Thakur et al. | |
| 2017/0281095 A1 | 10/2017 | An et al. | |
| 2017/0290550 A1* | 10/2017 | Perschbacher | A61B 5/076 |
| 2018/0064360 A1 | 3/2018 | Siejko et al. | |
| 2018/0104502 A1 | 4/2018 | Perschbacher et al. | |
| 2018/0192902 A1 | 7/2018 | Perschbacher et al. | |
| 2019/0232067 A1 | 8/2019 | Mahajan et al. | |

FOREIGN PATENT DOCUMENTS

| | | |
|---|---|---|
| EP | 3746176 B1 | 3/2023 |
| WO | WVO-2019152383 A1 | 8/2019 |

OTHER PUBLICATIONS

"U.S. Appl. No. 16/260,947, Advisory Action mailed Oct. 25, 2021", 4 pgs.

"U.S. Appl. No. 16/260,947, Examiner Interview Summary mailed Feb. 10, 2022", 3 pgs.

"U.S. Appl. No. 16/260,947, Examiner Interview Summary mailed Jun. 3, 2021", 3 pgs.

"U.S. Appl. No. 16/260,947, Final Office Action mailed Aug. 4, 2021", 19 pgs.

"U.S. Appl. No. 16/260,947, Non Final Office Action mailed Mar. 1, 2021", 23 pgs.

"U.S. Appl. No. 16/260,947, Non Final Office Action mailed Dec. 7, 2021", 25 pgs.

"U.S. Appl. No. 16/260,947, Notice of Allowance mailed Jun. 27, 2022", 8 pgs.

"U.S. Appl. No. 16/260,947, Response filed Mar. 7, 2022 to Non Final Office Action mailed Dec. 7, 2021", 14 pgs.

"U.S. Appl. No. 16/260,947, Response filed Jun. 1, 2021 to Non Final Office Action mailed Mar. 1, 2021", 18 pgs.

"U.S. Appl. No. 16/260,947, Response filed Oct. 4, 2021 to Final Office Action mailed Aug. 4, 2021", 11 pgs.

"European Application Serial No. 19705029.7, Response filed Mar. 12, 2021 to Communication pursuant to Rules 161(1) and 162 EPC mailed Sep. 9, 2021", 26 pgs.

"International Application Serial No. PCT/US2019/015603, International Preliminary Report on Patentability mailed Aug. 13, 2020", 7 pgs.

"International Application Serial No. PCT/US2019/015603, International Search Report mailed Apr. 1, 2019", 5 pgs.

"International Application Serial No. PCT/US2019/015603, Written Opinion mailed Apr. 1, 2019", 5 pgs.

\* cited by examiner

SYSTEMS AND METHODS FOR PRESENTING ARRHYTHMIA EPISODES

CLAIM OF PRIORITY

This application is a continuation of U.S. patent application Ser. No. 16/260,947, filed on Jan. 29, 2019, now U.S. Pat. No. 11,491,337, which claims the benefit of priority under 35 U.S.C. § 119(e) of U.S. Provisional Patent Application Ser. No. 62/625,197, filed on Feb. 1, 2018, each of which is herein incorporated by reference in its entirety.

TECHNICAL FIELD

This document relates generally to automated patient management, and more particularly, to systems, devices and methods for managing medical event episodes detected by a medical device.

BACKGROUND

Implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IMDs may also provide therapies to treat or alleviate certain medical conditions, such as cardiac electrostimulation therapies to treat cardiac arrhythmia or to rectify cardiac dyssynchrony in CHF patients.

The IMDs may generate patient alert notification upon a detection of a particular health condition or a medical event, such as a cardiac arrhythmia or worsening heart failure (WHF). Some IMIDs may register a patient-triggered episode of a medical event, and record physiologic data in response to the patient trigger. The alert notification may be provided to a healthcare provider to signal the patient health condition. Upon being notified, the healthcare provider may review the recorded physiologic data associated with the episode of medical event, determine the presence of or possible causes leading to the medical event, or assess whether a prescribed therapy has resulted in desired therapeutic outcome.

A patient management system may monitor patients with IMDs that are interconnected to the patient management via a data communication network. Such a patient management system may allow a healthcare provider to follow up with the patients remotely, or to assess device functions on a periodic basis.

OVERVIEW

A patient management system may manage a large volume of alert notifications corresponding to medical events reported by ambulatory medical devices (AMDs). For example, in managing a cohort of AMD patients in a clinic, the patient management system may frequently receive alert notifications on various cardiac arrhythmia episodes or worsening heart failure (WHF) events detected by the implantable cardiac devices, such as a cardiac monitor, a pacemaker, an implantable defibrillator, or a cardiac resynchronization therapy device. Some AMDs may register patient-triggered episodes such as when the patient demonstrates certain signs or symptoms, or experiences a precursor event indicative of a medical event (e.g., cardiac arrhythmia, syncope, or WHF events). Physiologic data associated with the device-detected medical events or patient-triggered episodes may be stored in an AMD, transmitted to a patient management system, and reviewed by a clinician for the purpose of, for example, adjudicating the device-detected medical events, scheduling patient follow-up visits, or reprogramming the AMDs, among others.

With a large number of AMDs connected to the patient management system, reviewing the device-detected medical events, such as detected cardiac arrhythmia episodes, may require significant amount of time and clinical, technical, and human resources, and can be costly or otherwise time consuming for a healthcare facility. Also, device-detected medical events may be of different degrees of severity or clinical significance. For example, some medical events may contain diagnostic information not presented in patient historical medical events or not reviewed and evaluated by the clinician. Some patients may repeatedly get false alerts of medical events (also known as false positive, or FP, detections) inappropriately detected by an AMD for the same or similar underlying causes. For example, in some patients, repeated FP detection of atrial tachyarrhythmia episodes may be attributed to premature ventricular contractions (PVCs), premature atrial contractions (PACs), or atrioventricular conduction abnormality such as Wenckebach atrioventricular block, among other causes. If these underlying causes are not timely recognized, FP detections with the same or similar causes may repeatedly trigger alert notifications, demanding additional time and resources for event review and adjudication. The present inventors have recognized a substantial challenge in efficient medical alert management, and particularly a need for systems and methods to automatically learn from previous FP detections, and re-evaluate, prioritize, and present alert notifications of the device-generated events or patient-triggered episodes. Such systems and methods may improve the efficiency of clinician review and adjudication of the medical events, and help align medical resources to serve those patients with critical medical conditions.

This document discusses, among other things, systems, devices, and methods for evaluating and prioritizing medical events generated by a medical device such as an AMD. An embodiment of a data management system includes a user interface to receive from the user an adjudication of a presented medical event episode. The adjudication includes an episode characterization characterizing the presented episode. The system includes a storage unit to store an association between a plurality of episode characterizations and corresponding detection algorithms for detecting a medical event having respective episode characterizations. An episode management circuit may detect from a subsequent episode, using the stored association, a medical event having an episode characterization of at least one medical event episode presented for adjudication, and schedule a presentation of at least a portion of the subsequent episode based on the detection. The system may program the medical device with a detection algorithm corresponding to the episode characterization of the presented episode.

Example 1 is a system for managing medical events generated by a medical device. The system comprises a user interface, a memory circuit, and an episode management circuit. The user interface may be configured to receive from a user an adjudication including an episode characterization characterizing a presented medical event episode. The memory circuit may be configured to store an association between one or more episode characterizations and one or more detection algorithms for detecting a medical event having respective episode characterizations. The episode management circuit may be configured to detect a medical event from a subsequent episode using a detection algorithm corresponding to the characterization of the medical event episode presented for adjudication, according to the stored association in the memory circuit.

In Example 2, the subject matter of Example 1 optionally includes the user interface that may be configured to present at least a portion of a first arrhythmia episode generated by the medical device and to receive from the user an adjudication decision and a first episode characterization of the first arrhythmia episode. The episode management circuit may be configured to: identify, from the stored association, a detection algorithm corresponding to the first episode characterization of the first arrhythmia episode; process a second arrhythmia episode using at least the identified detection algorithm to verify that the second arrhythmia episode has the first episode characterization; and schedule a presentation of at least a portion of the second arrhythmia episode based on a processing result of the second arrhythmia episode.

In Example 3, the subject matter of Example 2 optionally includes the adjudication decision that may include a user designation of presence or absence of an arrhythmia type in a first arrhythmia episode. The user interface may receive the episode characterization of the first arrhythmia episode if the adjudication decision indicates the first arrhythmia episode is a false-positive detection of the arrhythmia type.

In Example 4, the subject matter of Example 3 optionally includes the episode characterization that may include a user designation of a rationale for the adjudication decision.

In Example 5, the subject matter of any one or more of Examples 3-4 optionally includes the one or more episode characterizations stored in the memory circuit each representing a distinct rationale for an adjudication decision of an absence of the arrhythmia type.

In Example 6, the subject matter of Example 5 optionally includes the one or more episode characterizations including a premature ventricular contraction characterization. The associated detection algorithm includes a detection of atrial fibrillation based on a pair of consecutive decreases in ventricular heart rate.

In Example 7, the subject matter of any one or more of Examples 5-6 optionally includes the one or more episode characterizations including a premature atrial contraction characterization. The associated detection algorithm includes a detection of atrial fibrillation based on a cluster of ventricular heart beats.

In Example 8, the subject matter of any one or more of Examples 3-7 optionally include the episode management circuit that may be configured to detect the arrhythmia type from the second arrhythmia episode using the identified detection algorithm, and to schedule a presentation of the second arrhythmia episode only if the arrhythmia type is detected.

In Example 9, the subject matter of any one or more of Examples 2-8 optionally includes the episode management circuit that may be configured to identify a detection algorithm from the stored association including to modify a detection algorithm based on the first episode characterization, and process the second arrhythmia episode using at least the modified detection algorithm.

In Example 10, the subject matter of Example 9 optionally includes the modification of the identified detection algorithm including modifying a detection threshold.

In Example 11, the subject matter of any one or more of Examples 2-10 optionally includes an external device that may include one or more of the user interface, the memory circuit, and the episode management circuit. The external device may be configured to receive the arrhythmia episode from the medical device communicatively coupled to the external device.

In Example 12, the subject matter of Example 11 optionally includes the external device that may be configured to program the medical device with the identified detection algorithm corresponding to the episode characterization of a first arrhythmia episode.

In Example 13, the subject matter of Example 12 optionally includes the episode management circuit that may be configured to determine a prevalence indicator of the first episode characterization associated with the first arrhythmia episode using multiple arrhythmia episodes from a patient. The external device may be configured to program the medical device with the identified detection algorithm corresponding to the episode characterization if the determined prevalence indicator of the episode characterization satisfies a condition.

In Example 14, the subject matter of Example 13 optionally includes the prevalence indicator of the episode characterization including a count of adjudicated arrhythmia episodes that are designated with the episode characterization. The external device may be configured to program the medical device with the identified detection algorithm when the count exceeds a threshold.

In Example 15, the subject matter of any one or more of Examples 11-14 optionally includes the external device that may be configured to program the medical device to deliver therapy to treat arrhythmia.

Example 16 is a method for operating a medical system to manage medical event episodes generated by a medical device. The method comprises steps of: receiving from the user an adjudication including an episode characterization characterizing a first medical event episode; identifying, from a database of association between one or more episode characterizations and corresponding one or more detection algorithms for detecting a medical event having respective episode characterizations, a detection algorithm based on the received episode characterization; processing a second medical event episode, different from the first medical event episode, using at least the identified detection algorithm to verify that the second episode has the first episode characterization; and scheduling a presentation of at least a portion of the second medical event episode based on a processing result of the second medical event episode.

In Example 17, the subject matter of Example 16 optionally includes the first medical event episode including an arrhythmia episode, the adjudication includes an adjudication decision representing a user designation of presence or absence of an arrhythmia type, and the episode characterization including a user designation of a rationale for the adjudication decision. The episode characterization of the first arrhythmia episode may be received in response to the adjudication decision indicating the first arrhythmia episode is a false-positive detection of the arrhythmia type.

In Example 18, the subject matter of Example 17 optionally includes the plurality of episode characterizations in the database each representing a distinct rationale for an adjudication decision of an absence of the arrhythmia type.

In Example 19, the subject matter of any one or more of Examples 17-18 optionally includes identifying a detection algorithm from the stored association that may include modifying a detection algorithm based on the first episode characterization. The method further comprises processing the second arrhythmia episode using at least the modified detection algorithm.

In Example 20, the subject matter of Example 19 optionally includes modifying the identified detection algorithm including modifying a detection threshold.

In Example 21, the subject matter of any one or more of Examples 17-20 optionally includes steps of determining a prevalence of the first episode characterization associated with the first arrhythmia episode using multiple adjudicated arrhythmia episodes from a patient, and programming the ambulatory device with the identified detection algorithm corresponding to the episode characterization if the determined prevalence of the episode characterization satisfies a condition.

In Example 22, the subject matter of Example 21 optionally includes the prevalence of the episode characterization including a count of adjudicated arrhythmia episodes that are designated with the episode characterization. The ambulatory device may be programmed with the identified detection algorithm in response to the count exceeding a threshold The systems, devices, and methods discussed in this document may improve automated alert management in a patient monitoring system. As previously discussed, one of the challenges in medical alert management is that clinicians usually need to attend to a large amount of alert notifications. The present document provides a technological solution by automatically recognizing repetitive false positive event detections with the same or similarly underlying causes, reducing the number of alert notifications and prioritizing the alert notifications for clinical review and adjudication. Compared to conventional alert systems, the systems and methods discussed herein involve automated learning from previous false positive event detections, while preserving the capability of recognizing the true positive medical events that need to be reviewed, adjudicated, or otherwise attended. The systems and methods discussed herein therefore improve the accuracy of recognizing high-severity medical events and timely alerting clinicians of such an effect, yet at little to no additional cost or system complexity. Accordingly, the system and methods as described in the present document better align medical resources to serve those patients with critical medical conditions.

The medical event evaluation and prioritization discussed in this document may also improve the functionality of a patient management system. The medical event prioritization as discussed herein may be configured to evaluate and prioritize events reported by various medical devices. The event evaluation and prioritization may be implemented in, and executed by, a communicator, a mobile monitor, a programmer, or a remote patient management system in communication with an AMD. As such, in some cases, improved alert management may be achieved without modifying existing patient AMDs or medical event detectors. Because only medical events with higher priority and/or clinically more relevant to medical diagnosis may be stored in the system for clinician review or adjudication, the system memory usage may be more efficient than a traditional data management system. With fewer alerts and events for adjudication, complexity and operating cost of the patient management system can be reduced. Additionally, discussed herein includes systems and methods to adjust a detection algorithm implemented in the AMD based on user adjudication of a presented event episode, and program the adjusted detection algorithm into the AMD. Because the user adjudication provides additional information for better detecting the target medical events (e.g., arrhythmia events), the adjusted detection algorithm executed by and existing AMD may help reduce false positive detections. As a result, fewer unnecessary device therapy, drugs, and procedures may be scheduled, prescribed, or provided, battery life and longevity of the AMD can be extended, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for managing machine-generated alert notifications of medical events detected from one or more patients. An embodiment of a data management system may receive an adjudication of a medical event episode including an adjudication decision and an episode characterization. A storage unit to store an association between a plurality of episode characterizations and a plurality of detection algorithms for detecting a medical event having respective episode characterizations. An episode management circuit may detect from a target episode, using the stored association, a medical event having an episode characterization of at least one medical event episode presented for adjudication, and schedule presenting at least a portion of the target episode based on the detection.

Figure 1:
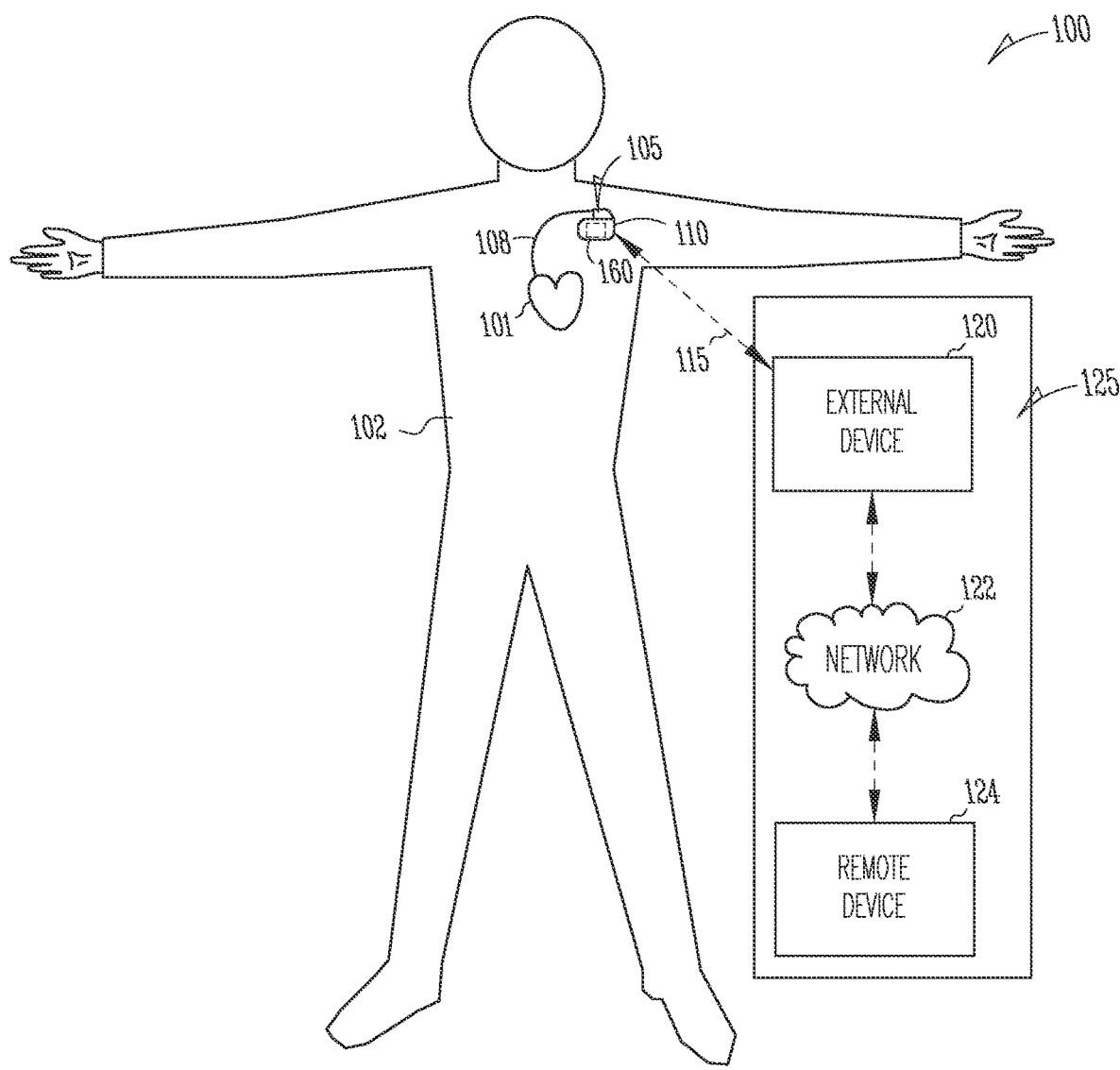
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a detector circuit 160 to detect a medical event using the sensed physiologic signals. In an example, the medical event includes a cardiac arrhythmia, such as atrial fibrillation, atrial flutter, atrial tachycardia, supraventricular tachycardia, ventricular tachycardia, or ventricular fibrillation, among other brady- or tachy-arrhythmia. In an example, the detector circuit 160 is configured to detect syncope, a presyncopal event or a precipitating event that may lead to a full-blown syncope. In some examples, the detector circuit 160 is configured to detect worsening of a chronic medical condition, such as worsening heart failure (WHF). The detector circuit 160 may execute a detection algorithm to monitor one or more physiologic signals continuously or periodically, and to detect the medical event automatically. Additionally or alternatively, the detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a medical event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event episodes, may be collected by the AMD 110, among other data acquisition sensors or devices associated with the patient 102. The remote device 124 may include a storage unit to store the patient data in a patient database. The storage unit may additionally store an association between a plurality of episode characterizations and a plurality of detection algorithms for detecting a medical event having respective episode characterizations. The server may process the device-generated event episodes to verify that a specific medical event (e.g., a cardiac arrhythmia type) is detected such that the device-detected event is a true positive (TP) detection; or that no such medical event is detected such that the device-detected event is a false positive (FP) detection. The processing of the device-generated medical event episodes may be based on a stored association. In an example, a first event episode may be presented to a user (e.g., a clinician), who would provide an adjudication decision and a first episode characterization. If the adjudication decision indicates that the first event episode is a FP detection, then the server may identify from the stored association a detection algorithm corresponding to the first episode characterization, and process a second event episode using at least the identified detection algorithm to determine that the second event episode is either a TP or a FP detection. The server may schedule a presentation of at least a portion of the second episode based on the processing result of the second episode. By using the detection algorithms tailored for recognizing episode with an episode characterization associated with a FP episode, more FP episodes having the same or similar episode characterization may be identified, and therefore avoided from being reviewed and adjudicated by the user. If the second event episode is determined to be a TP episode, then an alert is generated indicating further user review may be warranted.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a medical event prioritizer circuit configured to prioritize the alert notifications. For example, an alert of a detected medical event may be prioritized using a similarity metric between the physiologic data associated with the detected medical event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
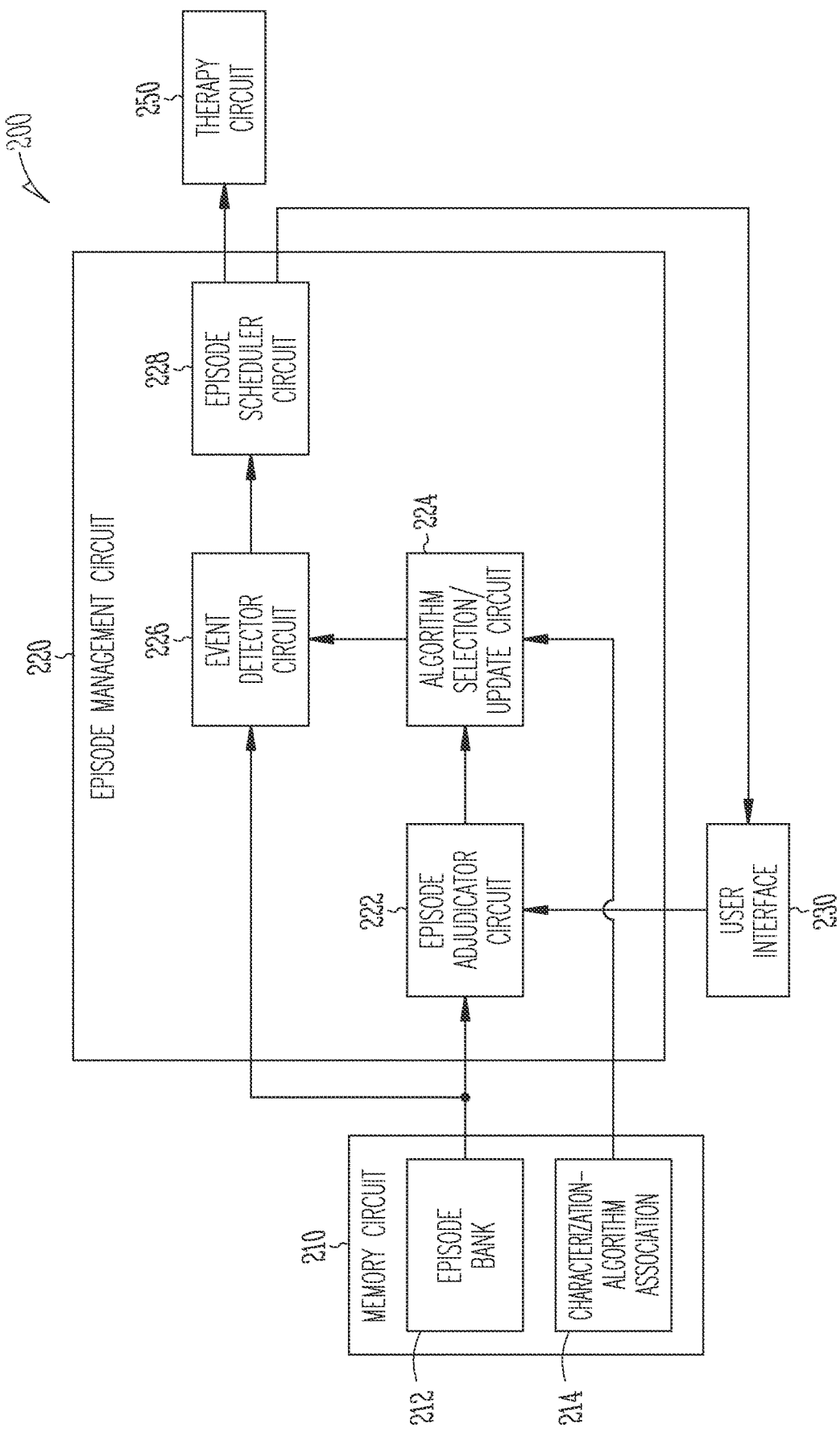
FIG. 2 illustrates generally an example of a medical event management system that may be configured to prioritize medical events detected by a medical device.

FIG. 2 illustrates generally an example of a medical event management system 200 configured to prioritize medical events detected by a medical device. At least a portion of the alert management system 200 may be implemented in the external system 125, such as one or more of the external device 120 or the remote device 124, or distributed between the AMD 110 and the external system 125. The alert management system 200 may include one or more of a memory circuit 210, an episode management circuit 220, and a user interface 230. The alert management system 200 may additionally be configured as a therapeutic system that includes an optional therapy circuit 250 for delivering a therapy.

The memory circuit 210 may store medical event episodes registered by a medical device, such as the AMD 110, in an episode bank 212. In an example, the memory circuit 210 may be communicatively coupled to the AMD 110, and receive the physiologic data from the AMD 110 through the communication link 115, as to be discussed in the following with reference to FIG. 3. The memory circuit 210 may be included in a storage device in the external system 125, such as within the external device 120, or the remote device 124. Alternatively, the memory circuit 210 may be included in an electronic medical record (EMR) system.

By way of example and not limitation, the medical event episodes stored in the episode bank 212 may include cardiac arrhythmia episodes, such as detected through dedicated circuits or processors in the AMD 110 that execute instructions to monitor one or more physiologic signals continuously or periodically. Examples of the cardiac arrhythmia episodes may include atrial arrhythmia episodes, supraventricular arrhythmia episodes, or ventricular arrhythmia episodes, among others. The cardiac arrhythmia episodes may include respective physiologic data sensed from one or more physiologic sensors during the detected arrhythmia event, or additionally physiologic data sensed before and/or after the detected arrhythmia event. The physiologic data associated with an arrhythmia episode may include cardiac electrical signals such as one or more electrogram (EGM) signals sensed at various cardiac sites using different electrode combinations, such as one or more atrial EGMs or one or more ventricular EGMs. Additionally or alternatively, the physiologic data may include cardiac mechanical signals or hemodynamic signals such as cardiac pressure signals, impedance signals, heart sounds signals, among others. In various examples, each cardiac arrhythmia episode may additionally include arrhythmia detection or classification generated by a medical device, such as the AMD 110. The arrhythmia detection or classification is a designation of a particular arrhythmia type, such as atrial fibrillation, atrial flutter, ventricular tachycardia, or ventricular fibrillation, among others. Other information about the cardiac arrhythmia episodes such as measurements or signal metrics obtained from the physiologic data (e.g., atrial rate, ventricular rate, variability of atrial or ventricular rate), may also be associated with respective episodes and stored in the episode bank.

In various examples, the episode bank 212 may include patient-triggered episodes of cardiac arrhythmia or other types of medical events. Information associated with the patient-triggered episode may include physiologic data sensed from one or more physiologic sensors in response to a patient trigger, such as when the patient experiences a medical event onset. Other information such as patient input about presence or absence of a medical event and severity of symptoms, timing information of the symptoms, such as onset and termination time of the patient-triggered episode, may also be associated with the patient-triggered episode and included in the episode bank 212.

The memory circuit 210 may include a characterization-algorithm association 214 that associate a plurality of episode characterizations with a plurality of detection algorithms that may be used to detect a medical event having respective episode characterizations. The characterization-algorithm association 214 may be implemented as a lookup table, an association map, or other data structures in the memory circuit 210. An episode characterization is a user designation of a rationale for an adjudication decision with respect to a medical event episode. Such a rationale may include diagnostic information, or one or more signal features of a medical event episode, that a clinician may use to form his or her adjudication decision. In an example, in reviewing a device-generated episode of atrial fibrillation (such as generated by the AMD 110), a clinician may adjudicate the arrhythmia episode as some arrhythmia type other than AF, or provide an adjudication decision of "FP" to indicate that the device erroneously detected the event as AF. The clinician may also designate an episode characterization, such as frequent premature atrial contraction (PACs), as a rationale for the "FP" adjudication decision.

The characterization-algorithm association 214 associates the episode characterization with a corresponding detection algorithm tailored to detect an arrhythmia event with the episode characterization. The algorithms associated with various episode characterizations may be distinct from each other. In an example, the various episode characterizations are each associated with respective detection parameters, such as distinct detection threshold values. In another example, the various episode characterizations are each associated with respective "add-on" algorithm features that may be incorporated into a common detection algorithm. By way of example and not limitation, Table 1 illustrates a portion of a characterization-algorithm association 214 between (1) various episode characterizations of those AF episodes detected by an AMD, and (2) the corresponding add-on algorithm features for detecting AF. The episode characterizations listed in Table 1 represent various rationales a user may use to reject the AF detection generated by the AMD. That is, the rationales correspond to user-designated causes of FP detection as made by the AMD 110.

TABLE 1

A portion of a characterization-algorithm association

| Episode Characterizations | Algorithm Features |
| --- | --- |
| Premature atrial contraction (PAC) | Cluster of ventricular heart beats |
| Premature ventricular contraction (PVC) | Consecutive decreases in ventricular heart rate |
| Wenckebach block or variable sinus rate | Wenchebach detector |
| Noise | SNR or signal quality |
| Stable rhythm at high rate | High rate correction |

As shown in Table 1, a premature atrial contraction (PAC) characterization is associated with an algorithm feature of a cluster of ventricular heart beats. The ventricular heart beat clusters, which may be characterized using a statistical distribution or a histogram of ventricular heart beats, represent regularity of ventricular contractions. Patients with AF are typically presented with irregular ventricular contractions. However, PACs may occur at irregular intervals, and when PAC conduct to the ventricle, they may produce irregular ventricular rate. A discriminator beyond irregularity may therefore help recognize PACs. The add-on feature of the ventricular heart beat cluster may be used to distinguish frequent PACs from an AF episode. Perschbacher et al. U.S. patent application Ser. No. 15/864,953 entitled "ATRIAL FIBRILLATION DISCRIMINATION USING HEART RATE CLUSTERING," refers to histogram clusters of ventricular rates and their use in discriminating between AF and non-AF events, the disclosure of which is incorporated by reference herein in its entirety.

Also shown in Table 1 is an association between a premature ventricular contraction (PVC) characterization and an algorithm feature of consecutive decreases in ventricular heart rate. The consecutive decrease in ventricular heart rate refers to a pair of consecutive ventricular rate changes in which both the first ventricular rate change and the second ventricular rate change of the pair are negative. Prevalence of the consecutive decrease, or double decrement, in ventricular heart rate may be used to detect atrial fibrillation. However, devoid of an ongoing AF rhythm, PVCs alone typically do not produce double decrement patterns in ventricular rate. As such, the algorithm feature of consecutive decrease in ventricular heart rate may be used to distinguish frequent PVCs from an AF episode. Krueger et al. U.S. patent application Ser. No. 14/825,669, entitled "ATRIAL FIBRILLATION DETECTION USING VENTRICULAR RATE VARIABILITY," refers to double decrement pattern in ventricular heart rate and its use in atrial arrhythmia detection, the disclosure of which is incorporated by reference herein in its entirety.

Table 1 also shows an association between a characterization of Wenckebach atrioventricular block or variable sinus rate and an algorithm feature of Wenckebach detector. Examples of the Wenckebach detector may be based on a repetitiveness indictor of various beat patterns of the cycle lengths or heart rates, such as discussed in Perschbacher et al. U.S. patent application Ser. No. 15/786,824 entitled "SYSTEMS AND METHODS FOR ARRHYTHMIA DETECTION," the disclosure of which is incorporated by reference herein in its entirety. Additionally, an episode characterization of noise may be associated to a signal-to-noise (SNR) detector or a signal quality detector, such as based on signal energy below a specified noise floor. The SNR or signal quality detector may differentiate the AF from noise. Table 1 further includes an association between an episode characterization of stable rhythm at high rate and an algorithm feature of high-rate correction of a detection parameter such as a detection threshold to account for potential sensing limitations at higher heart rates. The correction may be adjusted for variable R-wave detections at high heart rates.

The characterization-algorithm association may include additional "add-on" algorithm features for detecting other cardiac arrhythmias or events, such as a feature of "ventricular tachycardia detection algorithm" corresponding to an episode characterization of over-sensing, or a feature of "brady pause detection algorithm" corresponding to an episode characterization of under-sensing. Examples of brady pause detection may be based on a delay in ventricular depolarization and signal-to-noise metrics of the signal for a candidate pause episode, such as discussed in Siejko et al. U.S. patent application Ser. No. 15/697,756 entitled "BRADY PAUSE DETECTION FOR IMPLANTABLE CARDIAC MONITORS," the disclosure of which is incorporated by reference herein in its entirety.

The characterization-algorithm association 214 may be established and updated dynamically. In an example, a user (e.g., a clinician) may adjust an existing detection algorithm associated with a particular episode characterization, such as by increasing or decreasing a detection threshold parameter. In an example, a user may delete an existing episode characterization along with the associated detection algorithm. In another example, a user may add a new episode characterization different from any existing episode characterization, along with an associated detection algorithm or designated modification of one or more detection parameters. The characterization-algorithm association 214 may be dynamically updated when a user reviews and adjudicates a medical event episode, such as via the user interface 230. Examples of episode adjudication and update of characterization-algorithm association are discussed below, such as with reference to FIG. 4.

Although the discussion of medical events management in this document is focused on cardiac arrhythmia episodes, this is meant to be illustrative rather than restrictive in nature or limiting in any way. Episodes of other types of medical events, such as syncope, worsening heart failure events, or heart failure decompensation events, may also be stored, analyzed, and provided to a clinician for adjudication using the systems, apparatus, and methods discussed in this document.

The episode management circuit 220 may be implemented as parts of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The episode management circuit 220 may include circuit sets comprising one or more other circuits or sub-circuits, including an episode adjudicator circuit 222, an algorithm selection/update circuit 224, an event detector circuit 226, and an episode scheduler circuit 228. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The episode adjudicator circuit 222 may be coupled to the memory circuit 210 to process user input regarding adjudication of a medical event episode retrieved from the episode bank 212. Information of a medical event episode, including at least a portion of physiologic data collected during, and optionally before and/or after, the detection, as well as the detection results generated by the AMD, may be displayed on a display unit of the user interface 230. In an example, at least a portion of the user interface 230 may be implemented in the external system 125. The user interface 230 may include an input device that allows a user to provide episode adjudication, including an adjudication decision and an episode characterization. An adjudication decision may include a user designation of presence or absence of a specific medical event. In an example, the adjudication decision is a user designation of an arrhythmia type, such as an atrial fibrillation, atrial flutter, supraventricular tachycardia, ventricular tachycardia, or ventricular fibrillation. The episode adjudicator circuit 222 may compare the user designation of arrhythmia type to the detection result generated by the AMD, and identify the episode as a true positive (TP) detection if the user designation is in agreement with the detection result generated by the AMD, or a false positive (FP) detection if the user designation is different from the detection result generated by the AMD. In some examples, the adjudication decision may include a designation of a TP or a FP decision.

When reviewing a device-detected medical event episode (e.g., an arrhythmia episode), a user may provide an episode characterization along with the episode characterization such as via the user interface 230. The episode characterization represents a user-designated rationale for the adjudication decision, and may include diagnostic information, or one or more signal features of a medical event episode. For example, when adjudicating a device-detected AF episode, a user (e.g., a clinician) may designate one of a plurality of episode characterizations, such as those illustrated in Table 1, as a rationale for forming his or her adjudication decision. The plurality of episode characterizations may be pre-determined, and displayed on the display unit of the user interface 230, from which a user may select one that characterizes the episode at display. Additionally or alternatively, a user may enter the rationale for the adjudication decision, such as by adding a new episode characterization different from the existing episode characterizations.

In some examples, the user may be prompted to select or otherwise enter an episode characterization if the adjudication decision differs from the device-generated detection decision, or a "FP" adjudication decision is provided. The detection algorithm associated with that episode characterization may be determined from the characterization-algorithm association 214, and used to recognize device-detected event episodes in the episode bank 212 that have similar characterization to the FP episode that has been adjudicated.

The algorithm selection/update circuit 224, coupled to the episode adjudicator circuit 222 and the memory circuit 210, may select a detection algorithm using the characterization-algorithm association 214 and the episode characterization designated by the user. For example, according to Table 1, if a "PVC" is selected or otherwise provided by the user as the episode characterization for the arrhythmia episode at display, the corresponding add-on arrhythmia detection feature of "consecutive decreases in ventricular heart rate" may be incorporated into an AF detection algorithm. In some examples where the various episode characterizations in the characterization-algorithm association 214 are each associated with respective detection parameters (e.g., detection threshold values) of a common detection algorithm, the algorithm selection/update circuit 224 may select or adjust a detection parameter corresponding to the episode characterization designated by the user.

The event detector circuit 226 may process one or more of the event episodes in the episode bank 212 that have not been displayed and adjudicated using the selected or updated algorithm. The event detector circuit 226 may verify that said event episodes each have, or do not have, the episode characterization, and designate those event episodes as TP or FP episodes. For example, when the add-on arrhythmia detection feature of "consecutive decreases in ventricular heart rate" is selected, an AF detection algorithm with this add-on feature may be applied to one or more arrhythmia episodes stored in the episode bank 212. In an example, the event detector circuit 226 may process all the un-adjudicated event episodes in the episode bank 212 automatically each time when an algorithm is selected or updated by the algorithm selection/update circuit 224. In another example, the event detector circuit 226 operates in a command mode to process one or more un-adjudicated event episodes specified by the user.

The episode scheduler circuit 228 may schedule a presentation of one or more of the events episodes for adjudication based on the processing results of said event episodes using the selected or updated detection algorithm. The add-on arrhythmia detection feature may help recognize device-detected event episodes in the episode bank 212 that have similar characterization to the adjudicated FP episode, and thereby reducing the burden and cost of adjudicating FP episodes with the same or similar characterization. The scheduler circuit 228 may withhold presentation of FP episodes for adjudication, or alternatively assign low priorities to the FP episodes for adjudication, but assign high priorities to TP episodes for adjudication. In an example, the scheduler circuit 228 may rank a plurality of the event episodes in the episode bank 212 in a specified order of priority, and present one or more of the ranked plurality of event episodes to a user or a process. In an example, the event episodes may be presented in a descending order of the priority.

The user interface 230, as discussed previously, may include a display unit for displaying event episode for adjudication, and a plurality of selectable episode characterizations. Additionally, the display unit may present a recommendation for adjusting AMD programming. The user interface 230 may be coupled to a printer for printing hard copies of the detection information. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the user about the detected medical events. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the user about the detected medical events. In some examples, the user interface 230 may additionally generate a recommendation for adjusting AMD programming, such as by programming to the AMD one or more detection algorithms in the characterization-algorithm association 214.

The optional therapy circuit 250 may be configured to deliver a therapy to the patient in response to the detection of target medical event. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 250 may modify an existing therapy, such as adjust a stimulation parameter or drug dosage.

Figure 3:
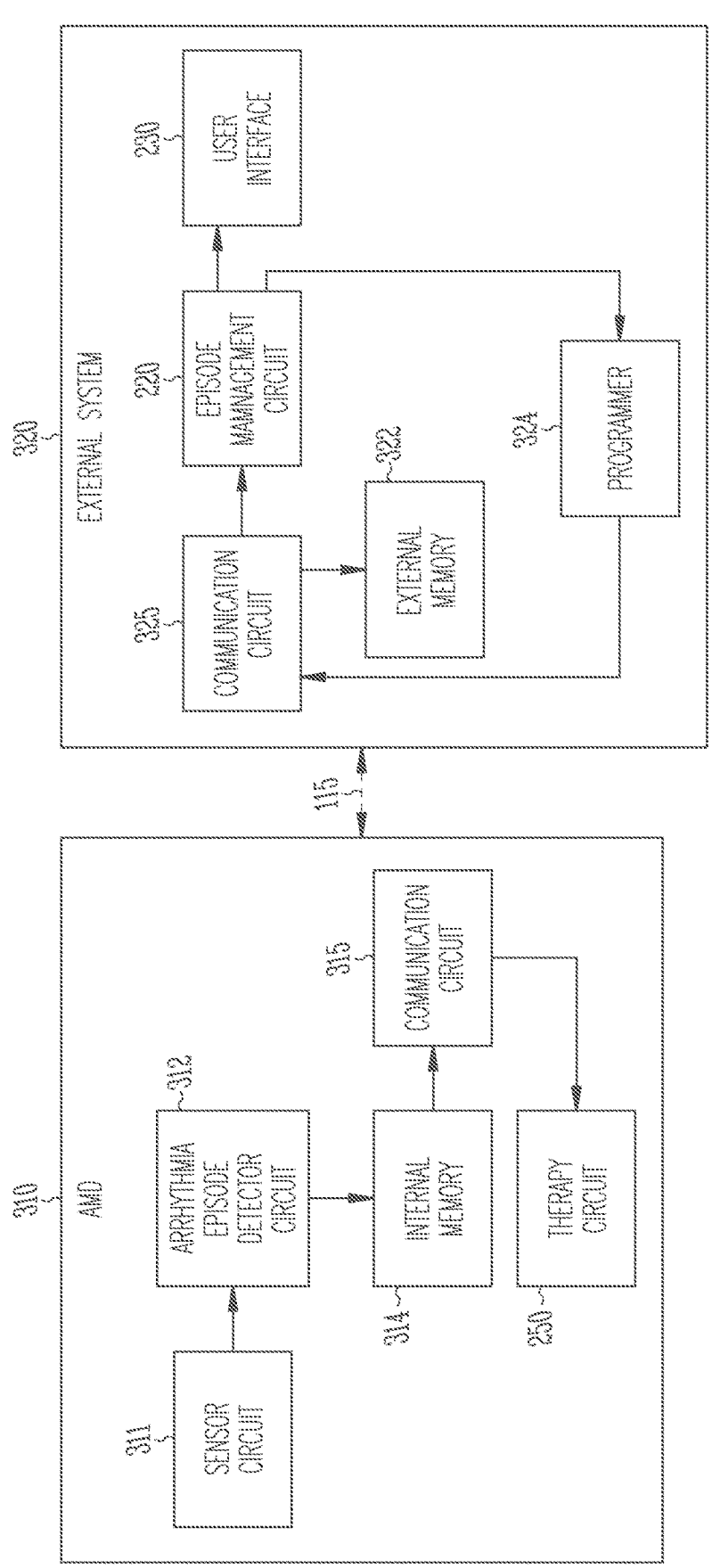
FIG. 3 illustrates generally an example of an arrhythmia management system configured to evaluate and prioritize patient alerts of medical events detected from one or more patients.

FIG. 3 illustrates generally an example of an arrhythmia management system 300 configured to evaluate and prioritize patient alerts of medical events detected from one or more patients. The alert management system 300 comprises an AMD 310 and an external system 320, communicatively coupled to each other via the communication link 115.

The AMD 310, which is an embodiment of the AMD 110 illustrated in FIG. 1, may include a sensor circuit 311 for sensing one or more physiologic signals from a subject. The physiologic signals may be sensed via one or more implantable, wearable, or otherwise ambulatory sensors or electrodes associated with the patient. The sensors may be incorporated into, or otherwise associated with an ambulatory device such as the AMD 110. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 311 may include one or more sub-circuits to digitize, filter, or perform other signal conditioning operations on the received physiologic signal. In some examples, the sensor circuit 311 may register a patient-triggered episode. When the patient demonstrates certain signs or symptoms or experiences a precursor event indicative of a target medical event, a trigger may be produced and detected by a patient trigger detector. A detection of the patient trigger may activate the sensor circuit 311 to register the patient-triggered episode, and to acquire physiologic data such as one or more physiologic signals.

The arrhythmia episode detector circuit 312 may be configured to detect a cardiac arrhythmia using the sensed one or more physiologic signals. Examples of the cardiac arrhythmias may include an atrial fibrillation, atrial flutter, supraventricular tachycardia, ventricular tachycardia, or ventricular fibrillation. The detection may be based on timing or morphological features extracted from the one or more physiologic signals. In an example, the arrhythmia episode detector circuit 312 may detect a specific cardiac arrhythmia using a configurable detection algorithm, such that one or more detection algorithm features may be added or modified via a programming device. The detected arrhythmia episodes, including physiologic data collected during, or additionally before and/or after, the detection, as well as the detection results, may be stored in the internal memory 314.

The communication circuit 315 may transmit the detected arrhythmia episodes (including physiologic data and device-generated detection results) to the external system 320 via the communication link 115. The transmission may be carried out continuously, periodically at scheduled time, or in response to a data interrogation command sent to the AMD 310 from the external system 320. The external system 320, which is an embodiment of the external system 125, may receive the arrhythmia episodes via a communication circuit 325, and store the received arrhythmia episodes in an external memory 322. The external memory, which is an embodiment of the memory circuit 210, may store the arrhythmia episodes in the episode bank 212, and additionally maintain a characterization-algorithm association 214. The external system 320 also includes the episode management circuit 220 and the user interface 230. As discussed previously with reference to FIG. 2, the user interface 230 may be configured to display at least a portion of a first arrhythmia episode stored in the external memory 322 such as in response to a user command, and receive from the user an adjudication decision and a first episode characterization (C1) of the displayed episode. The episode management circuit 220 may identify, from the stored association, a detection algorithm (F1) corresponding to the characterization C1 of the first arrhythmia episode, and process one or more of arrhythmia episodes in the episode bank using at least the identified detection algorithm F1 to determine whether each of the processed arrhythmia episodes has the first episode characterization. The identified detection algorithm F1 may include an add-on arrhythmia detection algorithm feature as shown in Table 1, or one or more detection parameters such as a detection threshold value. The processing of the arrhythmia episodes can be carried out automatically or in a user command-mode. Based on the processing results, the episode management circuit 220 may schedule a presentation of one or more of the arrhythmia episodes for adjudication. In an example, the episode management circuit 220 may rank the arrhythmia episodes in a specified order of priority and presented to a user or a process according to the ranking order.

The external system 320 includes a programmer 324 that may generate commands for programming the AMD 310. The commands may include recommended adjustment of one or more detection parameters for the arrhythmia episode detector circuit 312, or data collection parameters for the sensor circuit 311, among others. The recommended adjustment may be confirmed or otherwise modified by a user (e.g., a clinician) via the user interface 230, and forwarded to the AMD 310 via the communication link 115.

In an example, the programmer 324 may program the AMD 310 with the identified detection algorithm F1 corresponding to the episode characterization of a first arrhythmia episode. Programming of the AMD 310 may be carried out if the first episode characterization C1 satisfies a specific condition. In an example, the episode management circuit 220 may determine a prevalence indicator of C1 based on the processing results of multiple arrhythmia episodes from a patient. The prevalence indicator indicates how frequent the episode characterization C1 is found to be present in the arrhythmia episodes being processed. In an example, the episode management circuit 220 may include a counter to count the arrhythmia episodes having the episode characterization C1. The prevalence indicator may be represented by the total count of the arrhythmia episodes having the episode characterization C1. For example, an arrhythmia episode (e.g., an AF episode detected by the AMD 310) may be processed using the detection algorithm F1. If AF is no longer detected, then the arrhythmia episode is considered to have the episode characterization C1, and is designated as a FP episode associated with the episode characterization C1, similar to the first adjudicated arrhythmia episode. The counter is then incremented. Where the count of the FP episodes corresponding to C1 in the counter exceeds a threshold, the user interface 230 may prompt a user to recommend programming the detection algorithm F1 to the AMD 310. Upon receiving a user confirmation, the programmer 324 and the communication circuit 325 may collaboratively deliver the detection algorithm F1 to the AMD 310 via the communication link 115. In an example, the detection algorithm F1 includes an add-on detection feature, and an existing detection algorithm in the AMD 310 may be modified to incorporate the add-on detection feature in F1. In another example, the detection algorithm F1 includes values of one or more detection parameters (e.g., a detection threshold), and an existing detection algorithm in the AMD 310 may be modified to incorporate the detection parameter values in F1. The AMD 310 may detect a target medical event using the modified algorithm.

Figure 4:
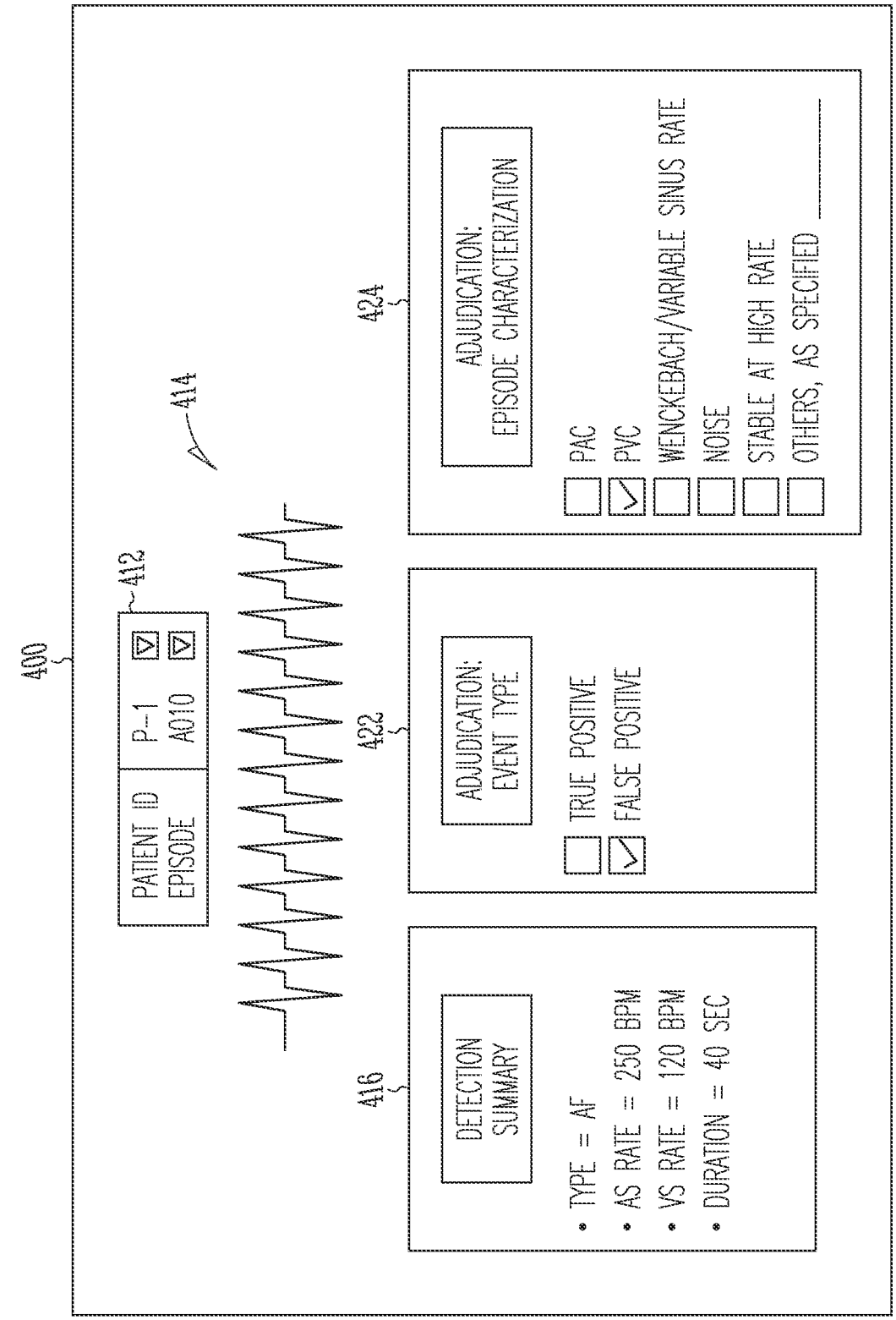
FIG. 4 illustrates an example of at least a portion of a user interface for displaying, and interactive user adjudication, of a medical event episode.

FIG. 4 illustrates an example of at least a portion of a user interface 400 for displaying, and interactive user adjudication, of a medical event episode. The user interface portion 400, which is an embodiment of the display unit of the user interface 230, includes a display of information of a medical event episode generated by a medical device, such as the AMID 310. By way of example and not limitation, the displayed information may include patient identification and episode identifier 412 and physiologic data 414. A user may interactively select a patient and an episode for display, such as by using respective drop-down lists (as shown), check boxes, radio buttons, list boxes, buttons, toggles, text fields, among other input control elements on the user interface 400. The physiologic data 414 may be sensed using electrodes or physiologic sensors in communication with the medical device, and collected during, or alternatively before or after, the detected medical event. In the example as illustrated in FIG. 4, the physiologic data 414 includes an electrogram sensed at a cardiac site, such as a ventricle or an atrium. In some examples, two or more physiologic signals may be displayed, including EGMs from multiple cardiac sites or via different sensing electrode configurations, cardiac mechanical signals, or hemodynamic signals sensed from one or more sensors. A marker channel including within-channel or inter-channel timing information or annotations of detected event (such as sensed or paced heart beats) may also be displayed. The displayed information of a medical event episode may additionally include a detection summary 416. By way of example, the detection summary may include type of medical event detected by the AMD (e.g., an AF), and measurements from the sensed physiologic signals as taken by the AMD (e.g., heart rate at various heart chambers or duration of the detected medical event).

The user interface portion 400 may include a display zone allowing for interface adjudication of the medical event as presented on the user interface portion 400. On an adjudication type zone 422, a user (e.g., a clinician) may provide an adjudication decision, such as an arrhythmia type, or a designation of a true positive detection (indicating an agreement with the device-detected arrhythmia type shown in the detection summary 416) or a false positive detection (indicating a disagreement with the device-detected arrhythmia type shown in the detection summary 416). On an episode characterization zone 424, the user may select an episode characterization from a plurality of pre-set characterizations. In an example, a user may be prompted to select an adjudication cause if a false positive adjudication decision is entered, or if the user-adjudicated event type is different from the device-detected event type. The episode characterizations represent various rationales for the adjudication decision. For example, FIG. 4 illustrates episode characterizations representing various rationales for rejecting a finding of AF in the arrhythmia episode in display, including PAC, PVC, Wenchebach block/variable sinus rate, noise, or stable at high rate, as discussed previously with reference to Table 1. A user may alternatively enter an episode characterization representing a rationale different from any of the given characterizations. The user input of the episode characterization may be used by the algorithm selection/update circuit 224 to select a detection algorithm according to a characterization-algorithm association, such as that illustrated in Table 1.

Figure 5:
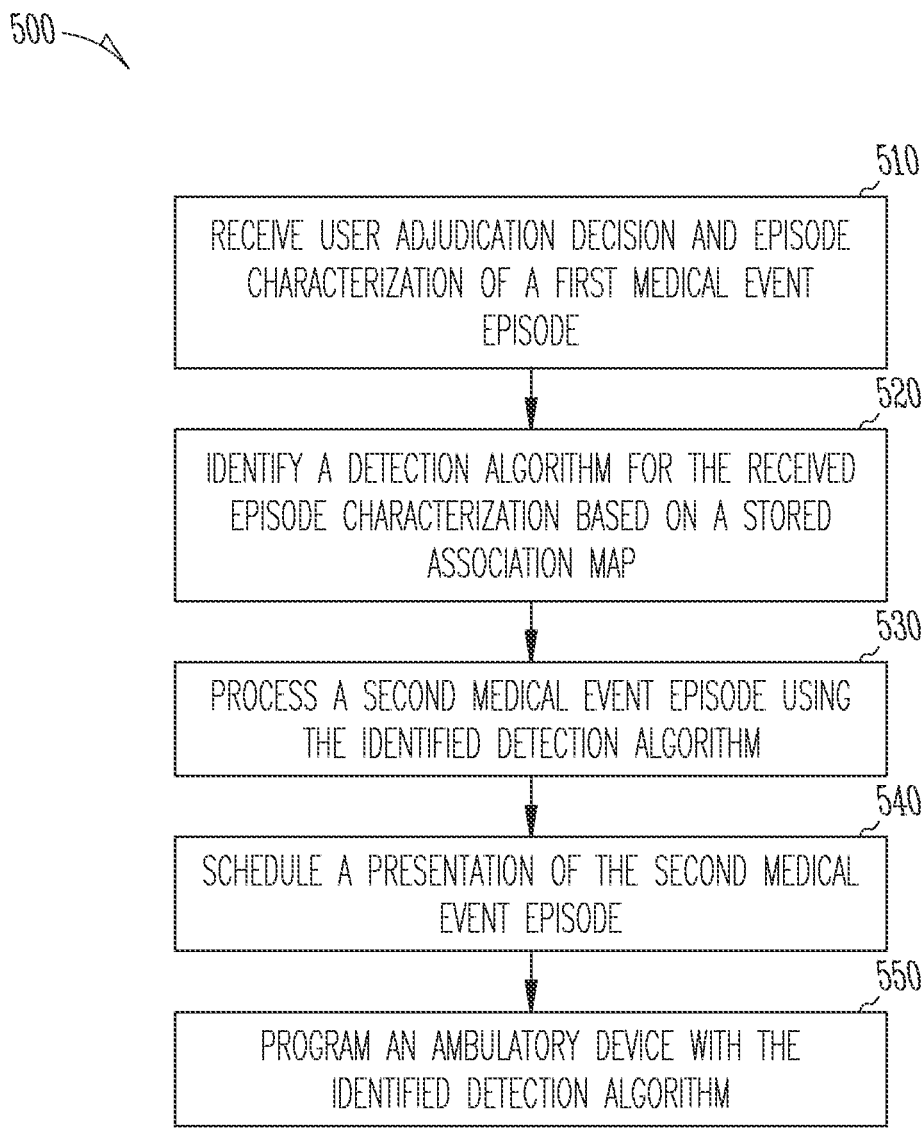
FIG. 5 illustrates generally an example of a method for detecting and reporting medical event episodes such as generated by an ambulatory medical device.

FIG. 5 illustrates generally an example of a method 500 for detecting and reporting medical event episodes such as generated by an ambulatory medical device. Examples of the medical event episodes include a specific cardiac arrhythmia, such as atrial fibrillation, atrial flutter, atrial tachycardia, supraventricular tachycardia, ventricular tachycardia, or ventricular fibrillation, among other brady- or tachy-arrhythmia. The method 500 may be implemented and executed in an ambulatory medical device such as an implantable or wearable medical device, or in a remote patient management system. In an example, the method 500 may be implemented in, and executed by, the AMD 110, one or more devices in the external system 125, or the medical event management system 200. Although the present document is focused on cardiac arrhythmia detection, the system and methods discussed herein, or variations thereof, may be used to detect and manage other medical events, such as syncope, presyncope, or a chronic medical condition such as a worsening heart failure (WHF) event.

The method 500 commences at 510, where a user adjudication of a first medical event episode, such as a cardiac arrhythmia episode detected by the AMD 110, may be received. The cardiac arrhythmia episode includes physiologic data sensed from one or more physiologic sensors during the detected arrhythmia event, or additionally physiologic data sensed before and/or after the detected arrhythmia event. The physiologic data associated with an arrhythmia episode may include cardiac electrical or mechanical signals or hemodynamic signals such as cardiac pressure signals, impedance signals, heart sounds signals, among others. The cardiac arrhythmia episode may additionally include arrhythmia detection or classification generated by a medical device. The arrhythmia detection or classification is a designation of a particular arrhythmia type, such as atrial fibrillation, atrial flutter, ventricular tachycardia, or ventricular fibrillation, among others. Other information about the cardiac arrhythmia episodes such as measurements or signal metrics obtained from the physiologic data (e.g., atrial rate, ventricular rate, variability of atrial or ventricular rate), may also be associated with respective episodes and stored in the episode bank.

Information about the first cardiac arrhythmia episode may be displayed on a display unit of the user interface 230. A user (e.g., a clinician) may inspect the first cardiac arrhythmia episode and provide user adjudication using, for example, the input control elements such as displayed on illustrated in FIG. 4. The adjudication may include an adjudication decision and an episode characterization. The adjudication decision may include a user designation of presence or absence of a specific medical event. In an example, the adjudication decision is a user designation of an arrhythmia type, such as an atrial fibrillation, atrial flutter, supraventricular tachycardia, ventricular tachycardia, or ventricular fibrillation. In some examples, the adjudication decision may include a designation of a TP decision (indicating an agreement between adjudication decision and the detection result generated by the AMD) or as a FP decisions (indicating a disagreement between adjudication decision and the detection result generated by the AMD). The episode characterization is a user designation of a rationale for the adjudication decision with respect to the first medical event episode. Such a rationale may include diagnostic information, or one or more signal features of a medical event episode, that a clinician may use in forming his or her adjudication decision. For example, in reviewing a device-detected arrhythmia episode (e.g., an AF episode), a clinician may make an adjudication decision of the arrhythmia episode as an arrhythmia type other than AF, or an adjudication decision of a FP detection inappropriately detected by the device, and a\n episode characterization of frequent premature atrial contraction (PACs), as a rationale for the adjudication decision of FP detection. Table 1 shows various episode characterizations as respective rationales for an adjudication decision of AF being absent from the device-detected episode, or an indication that the episode is an FP detection inappropriately detected by device.

At 520, a detection algorithm may be determined based on the received episode characterization. The determination of the detection algorithm may involve a database of association between a plurality of episode characterizations and a plurality of detection algorithms for detecting a medical event having respective episode characterizations. The characterization-algorithm association associates the episode characterization with a corresponding detection algorithm tailored to detect an arrhythmia event with the episode characterization. The algorithms associated with various episode characterizations may be different from each other. In an example, the various episode characterizations are each associated with respective detection parameters, such as distinct detection threshold values, of a common detection algorithm. In another example, the various episode characterizations are each associated with respective "add-on" algorithm features that may be incorporated into a common detection algorithm. Table 1 illustrates such a characterization-algorithm association between various characterizations of AF episodes detected by an AMD and the corresponding add-on algorithm features for detecting AF.

Using the characterization-algorithm association, a detection algorithm may be selected that corresponds to the received episode characterization. For example, according to Table 1, if a "PVC" is selected or otherwise provided by the user as the episode characterization for the arrhythmia episode at display, the add-on arrhythmia detection feature of "consecutive decreases in ventricular heart rate" may be selected and used in subsequent detection of other device-detected arrhythmia episodes. In some examples, a detection parameter (e.g., an arrhythmia detection threshold value) may be adjusted according to the episode characterization received from the user.

At 530, a second medical event episode, different from the first medical event episode, may be processed using at least the identified detection algorithm to verify that the second event episode has the first episode characterization presented in the first cardiac arrhythmia event, such as via the event detector circuit 226. For example, corresponding to an episode characterization "PVC" of the first arrhythmia episode, an add-on arrhythmia detection feature of "consecutive decreases in ventricular heart rate" may be selected according to the characterization-algorithm association show in Table 1. A detection algorithm with this add-on feature may be applied to the second arrhythmia episode. In an example, all of the un-adjudicated event episodes, such as those stored in the episode bank 212, may automatically be processed using the detection algorithm with this add-on feature.

At 540, a presentation of at least a portion of the second medical event episode may be scheduled, such as via the episode scheduler circuit 228, based on a processing result of the second medical event episode using the selected or updated detection algorithm. The add-on arrhythmia detection feature may help recognize those device-detected episodes that have similar characterization to the adjudicated FP episode, and thereby reducing the burden and cost of adjudicating FP episodes with similar characterization. In an example, if it is verified that the target medical event (e.g., AF) is no longer detected from the second event episode using the selected or updated detection algorithm, then the second event episode may be scheduled not to be presented to the user for adjudication, or alternatively be assigned a lower priority to that episode for adjudication. Conversely, if a target medical event (e.g., AF) is verified in the second event episode using selected or updated detection algorithm, then the second event episode may be scheduled to be presented to the user for adjudication, or alternatively be assigned a higher priority for adjudication. In an example, the event episodes in the episode bank 212 may be ranked in a specified order of priority, and be present to a user or a process. In an example, the event episodes may be presented in a descending order of the priority.

At 550, the identified detection algorithm may be programmed to the ambulatory medical device that generate the episodes stored in the episode bank 212, such as the AMD 310. The device programming may be carried out if the received episode characterization of the first medical event (denoted by C1) satisfies a specific condition. In an example, a prevalence indicator of C1 may be determined based on the processing results of multiple arrhythmia episodes from a patient. In an example, the prevalence indicator may be represented by the total count of the arrhythmia episodes having the episode characterization C1. For example, an arrhythmia episode may be processed using the identified detection algorithm. If AF is no longer detected, then the arrhythmia episode is designated as a FP episode, and the counter is then incremented. Where the count of the FP episodes corresponding to the episode characterization C1 in the counter exceeds a threshold, the identified detection algorithm may be programmed to the AMD, either automatically or upon a user confirmation. In an example, the identified detection algorithm includes an add-on detection feature, and an existing detection algorithm residing in AMD 310 may be modified to incorporate the add-on detection feature. In another example, the identified detection algorithm includes a particular value for a detection parameter such as a detection threshold, and an existing detection algorithm residing in the AMD 310 may be modified to incorporate the detection parameter value. The AMD may detect a target medical event using the modified algorithm.

Figure 6:
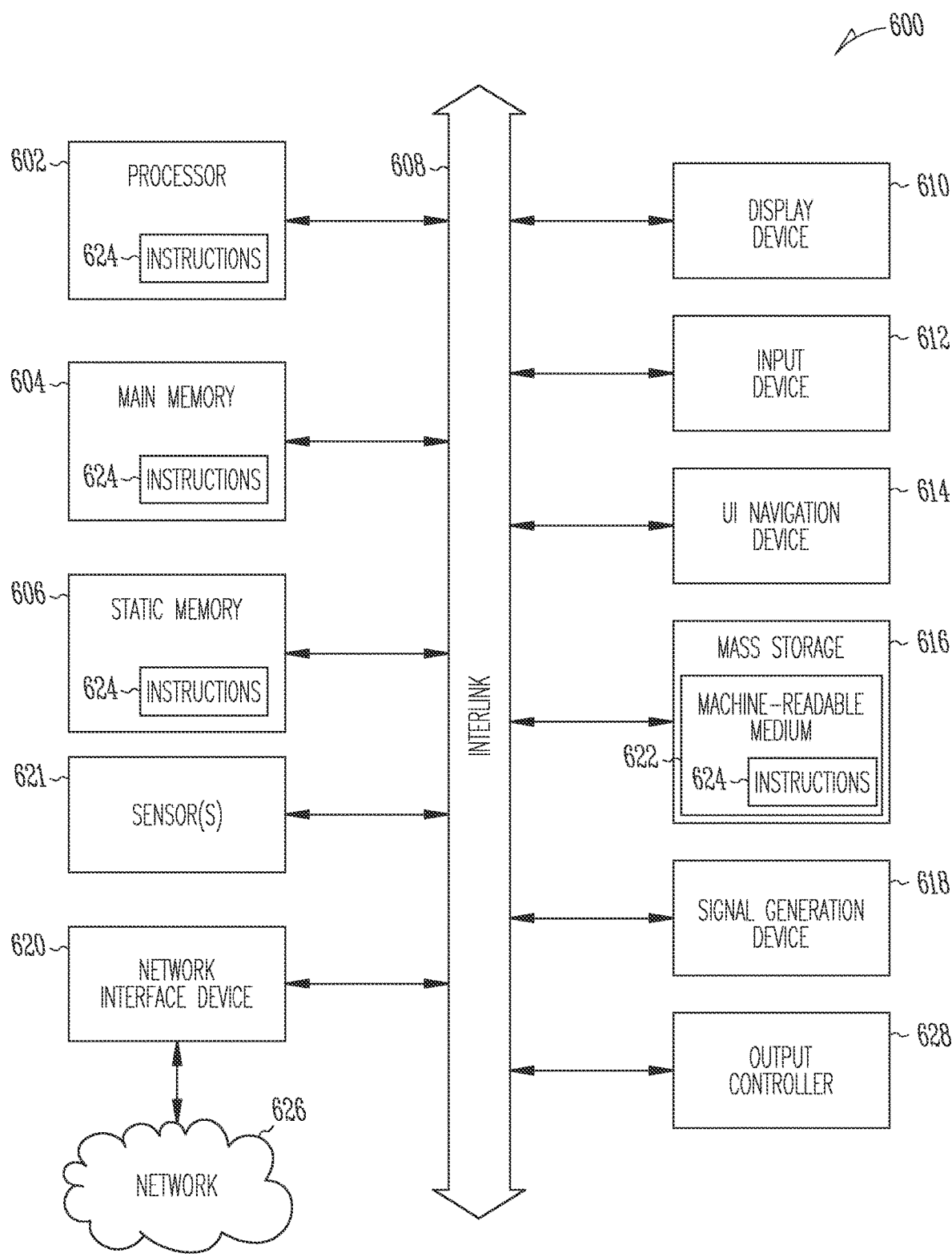
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communication network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communication network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for managing medical events generated by a medical device, the system comprising:
   a user interface configured to receive, from a user, an adjudication including an episode characterization characterizing a presented medical event episode;
   a memory circuit configured to store a database including one-to-one mapping between episode characterizations and detection algorithms for detecting a medical event having respective episode characterizations, wherein the one-to-one mapping maps each of the episode characterizations to a detection algorithm including a distinct algorithm feature; and
   an episode management circuit configured to:
      identify, from the stored detection algorithms, a detection algorithm that corresponds to the episode characterization of the medical event episode presented for adjudication according to the one-to-one mapping between the episode characterizations and the detection algorithms;
      determine a number of false positive adjudications of arrhythmia episodes of a patient for the episode characterization characterizing the presented medical event episode; and
      present the number of false positive adjudication and the detection algorithm corresponding to the episode characterization characterizing the presented medical event episode to the user on the user interface.

2. The system of claim 1, wherein the user interface is further configured to receive a user input to adjust the detection algorithm corresponding to the episode characterization characterizing the presented medical event episode, wherein the episode management circuit is configured to detect a medical event from a subsequent episode using the adjust detection algorithm.

3. The system of claim 2, wherein the user input to adjust the detection algorithm includes an adjustment of an arrhythmia detection threshold value, or an incorporation of a detection feature into the detection algorithm.

4. The system of claim 2, wherein the user interface is configured to receive the user input to adjust the detection algorithm in response to the number of false positive adjudications exceeding a threshold.

5. The system of claim 1, wherein the user interface is configured to:
   present at least a portion of an arrhythmia episode generated by the medical device; and
   receive from the user an adjudication decision of the presented arrhythmia episode and an episode characterization of the presented arrhythmia episode, the adjudication decision including a true position adjudication or a false positive adjudication based on user designation of a presence or absence of an arrhythmia type in the presented arrhythmia episode.

6. The system of claim 5, wherein the user interface is configured to receive the episode characterization of the presented arrhythmia episode in response to the adjudication decision indicates the presented arrhythmia episode is a false positive detection of the arrhythmia type.

7. The system of claim 1, wherein the episode management circuit is configured to:
   automatically adjust the detection algorithm corresponding to the episode characterization characterizing the presented medical event episode in response to the number of false positive adjudications exceeding a threshold; and
   detect a medical event from a subsequent episode using the automatically adjusted detection algorithm.

8. The system of claim 7, wherein the user interface is configured to receive from the user a confirmation or a modification of the automatically adjust detection algorithm,
   wherein the episode management circuit is configured to update the automatically adjusted detection algorithm based on the received confirmation or the modification.

9. The system of claim 1, wherein the episode characterizations in the database include respective rationales for adjudicating atrial fibrillation episodes, and the detection algorithms in the database include atrial fibrillation detection algorithms.

10. The system of claim 9, wherein the one-to-one mapping maps a premature ventricular contraction characterization to an atrial fibrillation detection algorithm based on a pair of consecutive decreases in ventricular heart rate.

11. The system of claim 9, wherein the one-to-one mapping maps a premature atrial contraction characterization to an atrial fibrillation detection algorithm based on a cluster of ventricular heart beats.

12. The system of claim 9, wherein the one-to-one mapping maps a Wenckebach block or variable sinus rate characterization to an atrial fibrillation detection algorithm based on a repetitiveness of a heartbeat pattern.

13. The system of claim 9, wherein the one-to-one mapping maps a stable rhythm at elevated rate characterization to an atrial fibrillation detection algorithm based on an adjusting heartbeat sensing threshold.

14. A method for operating a medical system to manage medical event episodes generated by a medical device, the method comprising:
   receiving, via a user interface, a user input of an adjudication including an episode characterization characterizing a presented medical event episode;
   accessing a memory circuit that stores a database including one-to-one mapping between episode characterizations and detection algorithms for detecting the medical event having respective episode characterizations;
   via an episode management circuit, identifying from the database a detection algorithm for the episode characterization presented for adjudication using an episode management circuit, wherein the one-to-one mapping maps each of the episode characterizations to a detection algorithm including a distinct algorithm feature;
   via the episode management circuit, determining a number of false positive adjudications of arrhythmia episodes of a patient for the episode characterization characterizing the presented medical event episode; and
   presenting the number of false positive adjudication and the detection algorithm corresponding to the episode characterization characterizing the presented medical event episode to the user on the user interface.

15. The method of claim 14, further comprising:
receiving a user input to adjust the detection algorithm corresponding to the episode characterization characterizing the presented medical event episode; and
detecting a medical event from a subsequent episode using the adjust detection algorithm.

16. The method of claim 15, wherein the user input to adjust the detection algorithm includes adjusting an arrhythmia detection threshold value, or incorporating a detection feature into the detection algorithm.

17. The method of claim 15, wherein receiving the user input to adjust the detection algorithm is in response to the number of false positive adjudications exceeding a threshold.

18. The method of claim 14, comprising:
presenting at least a portion of an arrhythmia episode generated by the medical device; and
receiving from the user an adjudication decision of the presented arrhythmia episode and an episode characterization of the presented arrhythmia episode, the adjudication decision including a true position adjudication or a false positive adjudication based on user designation of a presence or absence of an arrhythmia type in the presented arrhythmia episode.

19. The method of claim 14, comprising:
automatically adjusting the detection algorithm corresponding to the episode characterization characterizing the presented medical event episode in response to the number of false positive adjudications exceeding a threshold; and
detecting a medical event from a subsequent episode using the automatically adjusted detection algorithm.

20. The method of claim 14, wherein the episode characterizations in the database include respective rationales for adjudicating atrial fibrillation episodes, and the detection algorithms in the database include atrial fibrillation detection algorithms.

* * * * *